United States Patent [19]

Lawless

[11] Patent Number: 4,462,891
[45] Date of Patent: Jul. 31, 1984

[54] OXYGEN SENSOR AND HIGH TEMPERATURE FUEL CELLS

[76] Inventor: William N. Lawless, c/o CeramPhysics, Inc., P.O. Box 346, Westerville, Ohio 43081

[21] Appl. No.: 464,248

[22] Filed: Feb. 7, 1983

[51] Int. Cl.$^3$ .............................................. G01N 27/58
[52] U.S. Cl. .................................... 204/427; 204/426; 204/424; 204/421; 429/30; 429/32; 429/33; 429/191; 429/193; 501/134; 501/136; 501/152
[58] Field of Search ............... 204/421, 412, 424, 426, 204/427; 429/30, 32, 33, 191, 193; 501/134, 136, 152

[56] References Cited

U.S. PATENT DOCUMENTS 3,554,808 6/1971 Fischer et al. ......................... 429/32
4,207,159 6/1980 Kimura ........................... 204/426 X
4,231,231 11/1980 Lawless ................................. 62/514

FOREIGN PATENT DOCUMENTS 2632138 2/1977 Fed. Rep. of Germany ...... 204/427

OTHER PUBLICATIONS

Takashashi et al., "High oxide ion conduction in sintered oxides of the system Bi$_2$O$_3$-WO$_3$", 3 J. Appln. Electrochemistry 65 (1973).

Primary Examiner—G. L. Kaplan
Assistant Examiner—Nam X. Nguyen
Attorney, Agent, or Firm—Biebel, French & Nauman

[57] ABSTRACT

New oxygen ion conducting ceramic materials represented by the formulas Ni(Nb$_{1-x}$M$_x$)$_2$O$_{6-x}$ and Ni$_2$(Nb$_{1-x}$M$_x$)$_2$O$_{7-x}$, wherein M is selected from the group consisting of Zr$^{+4}$, Ti$^{+4}$, Sn$^{+4}$, Sm$^{+4}$, Hf$^{+4}$ and Ce$^{+4}$ and x is a value from 0 to 0.2, are disclosed. These materials, along with Bi$_2$O$_3$ in solid solution with Y$_2$O$_3$ or Nb$_2$O$_5$, may be used in a sensor for determining the oxygen partial pressure of a first gas relative to the oxygen partial pressure of a second gas. The oxygen sensor includes a plurality of layers of the ceramic material and of layers of a porous metallic conductor are arranged to form a body having alternating ceramic and metallic layers, with first alternate ones of the metallic layers being exposed along one side of the body and second alternate ones of the metallic layers being exposed along an opposite side of the body. An electrode connects the first alternate metallic layers, and a second electrode connects the second alternate metallic layers. The device may also be used as a fuel cell, and a method of constructing the device is disclosed.

18 Claims, 6 Drawing Figures

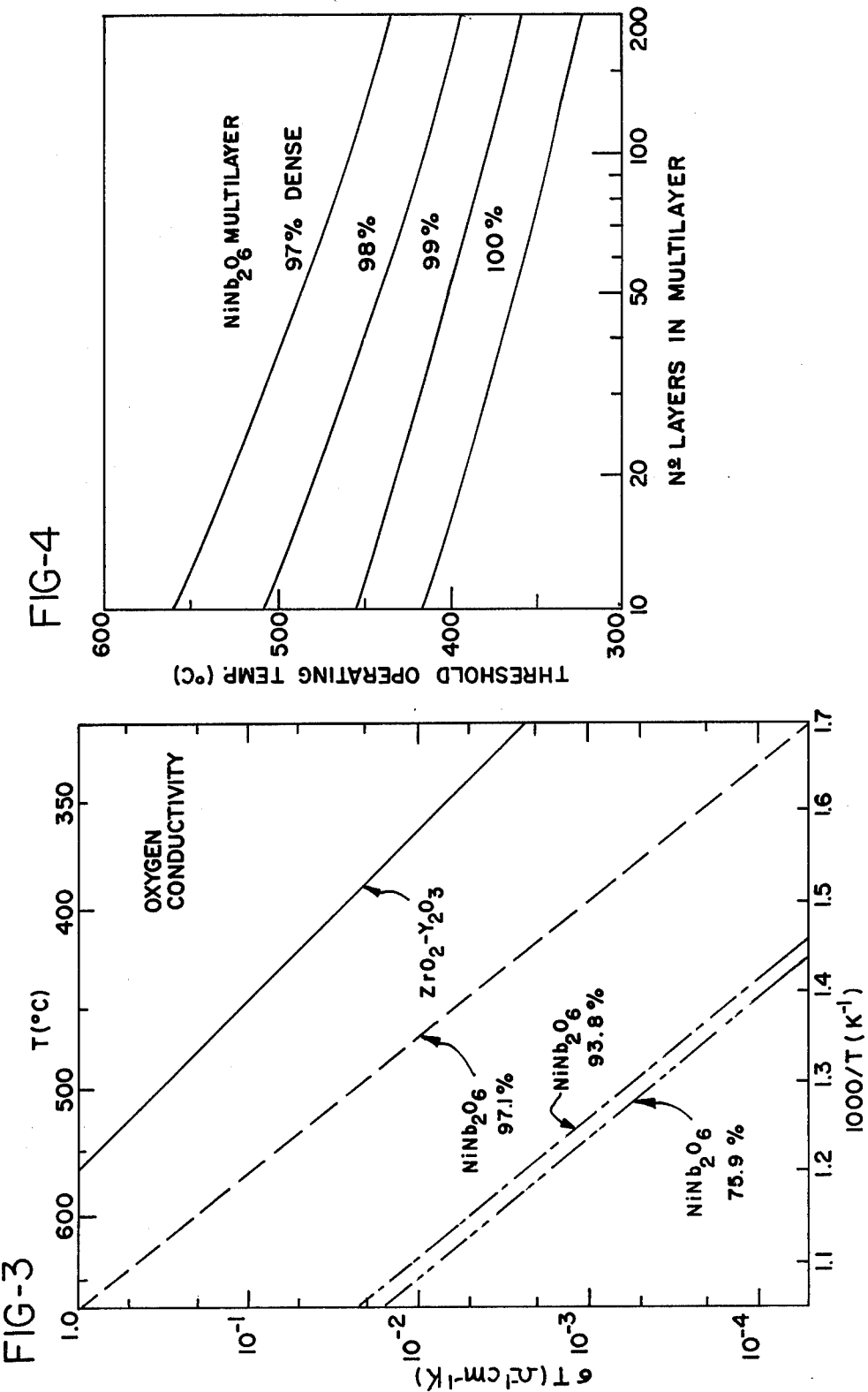

OXYGEN SENSOR AND HIGH TEMPERATURE FUEL CELLS

BACKGROUND OF THE INVENTION

The present invention relates to oxygen ion conductors and, more particularly, to such a device for sensing oxygen partial pressure in a first gas relative to a known oxygen partial pressure in a second gas, as well as for use as a fuel cell.

Because oxygen is an essential element of combustion processes, it is helpful to use oxygen sensors to monitor the exhaust gases of the combustion. Optimum fuel efficiency of a flame requires the correct oxygen-to-fuel ratio, since too little oxygen results in wasted, unburned fuel. Moreover, too great an oxygen concentration also wastes fuel, since energy is used to heat the excess oxygen to the exit gas temperature. This problem is compounded, since air is generally used as a source of oxygen in combustion processes, consisting approximately of 20% oxygen and 80% nitrogen by volume. For each unit volume of excess oxygen heated to the flame temperature, four units of nitrogen must be heated as well.

The energy savings potential available through the use of oxygen sensors is well known. Presently known sensors function by monitoring the EMF developed across an oxygen ion conductor which is exposed to different partial pressures of oxygen.

Oxygen tends to move from a gas containing a high concentration of oxygen to one of lower concentration. If the two gases are separated from each other by an oxygen ion conductor, the oxygen molecules will dissociate on one surface of the conductor and absorb electrons to form oxygen ions. These ions can then diffuse through the ionic conductor, leaving the entry surface with a deficiency of electrons. On the exit or low oxygen concentration side of the conductor, oxygen ions leaving the material must give up electrons to form molecular oxygen, leaving the exit surface with an excess of electrons. Thus, an electrical potential difference, or EMF, is set up between the two surfaces of the ion conductor. The greater the difference in oxygen content of the two gases, the greater will be the tendency of oxygen to diffuse through the conductor, and the greater will be the potential difference between the entry and exit surfaces.

The EMF generated by the difference in partial pressures may be calculated by the Nernst relation:

$$EMF = t_i(RT/nF) \ln(P_{O_2}/P'_{O_2}) \qquad (1)$$

where $t_i$ is the ionic transference number, R is the gas constant, T is the absolute temperature, n is the number of electrons involved in the electrode reaction, F is the Faraday constant, and $P_{O_2}$ and $P'_{O_2}$ are the oxygen partial pressures in the first and second gases, respectively. In the present case, the electrode reaction is $O_2 + 4e^- \rightarrow 2O^{-2}$, and thus $n=4$.

A common known oxygen sensor is disclosed in A. M. Chirino and R. T. Sproule, "Application of High and Low Temperature Direct Continuous Oxygen Sensors", 59 Am. Ceramic Soc. Bull. 605 (1980). The oxygen ion conductor material used therein is a solid solution of $ZrO_2$ and approximately 8% by weight $Y_2O_3$. The addition of the $Y_2O_3$ to the $ZrO_2$ provides vacant oxygen sites in the material which are necessary for diffusion of the oxygen ions. The stabilized $ZrO_2$ is formed into the shape of a tube closed at one end, the tube typically being approximately ⅜ inch (1 cm) in diameter with wall thickness of 0.050 inches (0.125 cm) and 6 inches (15 cm) in length. The outer surface of the tube is exposed to the combustion exhaust gases, generally having a low oxygen content. The inner surface is simultaneously exposed to a reference atmosphere, usually atmospheric air, containing a higher oxygen content. Both surfaces of the tube are covered with a porous platinum metal coating which allows the gaseous oxygen to reach the $ZrO_2$ and provides an electrical contact for measurement of the generated EMF.

Calcia-stabilized $ZrO_2$ tubes have also been constructed, although the yttria-stabilized tubes are preferred due to their higher ionic conductivity and lower activation energy. Similarly, the use of ceria ($CeO_2$) ceramic tubes has also been studied.

There are several disadvantages to the $ZrO_2$ and $CeO_2$ electrolyte tubes. Raw material costs are relatively high, particularly in the case of yttria-stabilized $ZrO_2$. Moreover, very high temperatures are required for the ceramic processing of $ZrO_2$ and $CeO_2$, which have melting points of 2700° C. and 2600° C., respectively. The combination of these two disadvantages results in relatively high tube costs.

The long term usefulness of the zirconia-based electrolytes may be lost due to destabilization or the growth of monoclinic grains into the fluorite grains, either of which leads to degraded signal output. Additionally, the geometry of the tube leads to large internal resistances in the sensor requiring that the electrolytes be heated to approximately 600° C. to reduce the internal resistance below the external load resistance. Moreover, the entire, platinum-coated outer surface of the electrolyte tube is exposed to the exhaust gas which can result in undesirable corrosion and/or erosion problems; and the relatively small thermal conductivity of the stabilized zirconia can lead to thermal shock problems on thermal cycling, particularly with large tubes.

What is needed, therefore, is an oxygen sensor that is relatively inexpensive to manufacture, has a relatively long useful life, and requires a lower threshold operating temperature. The sensor should also be less susceptible to corrosion and/or erosion attack on the precious-metal electrodes, and should possess a high resistance to thermal shock.

SUMMARY OF THE INVENTION

The present invention meets this need by providing an oxygen sensor generally of the oxygen ion conducting type. The ceramic materials used in the sensor may be represented by the following formulas:

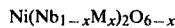

or

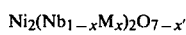

where M is selected from the group consisting of $Zr^{+4}$, $Ti^{+4}$, $Sn^{+4}$, $Sm^{+4}$, $Hf^{+4}$, $Ce^{+4}$ and mixtures thereof, and where x is a value from 0 to 0.2. Additionally, the ceramic material may be $Bi_2O_3$ in solid solution with either $Y_2O_3$ or $Nb_2O_5$.

A preferred electrolytic ceramic material for use in the sensor is $NiNb_2O_6$, which may be produced by mixing $Nb_2O_5$ and NiO in appropriate amounts. The mixture is then calcined for approximately two hours at 1000° C., and sintered for approximately one hour at 1350° C. However, all of the above ceramic materials are useful in the practice of the present invention.

Such a sensor, for determining the oxygen partial pressure of a first gas relative to the oxygen partial pressure of a second, reference gas, includes at least two layers of a porous metallic conductor. A layer of the ceramic material of the present invention is disposed between the metallic layers to form at least a portion of a solid body for the sensor. Individual electrodes are connected to each of the metallic layers, and the sensor is located relative to the gases so that one layer is exposed to the first gas, and the second layer is exposed to the second, reference gas. The porous metallic layers may be made of platinum or other suitable metal.

The oxygen sensor may also include a plurality of layers of the electrolytic ceramic material. A plurality of layers of a porous metallic conductor are provided, and each metallic layer is interposed between and contained by two of the ceramic layers to form a solid body of alternating ceramic and metallic layers. The body has first and second opposing sides, and first alternate ones of the metallic layers are exposed along the first side of the body, while second alternate ones of the metallic layers are exposed along the second side. A first electrode connects the first alternate metallic layers, and a second electrode connects the second alternate metallic layers.

The sensor may be in an environment wherein the first and second gases are separated by a baffle disposed between the two. The sensor body may be mounted through the baffle such that the first side of the body is exposed to the first gas, and the second side of the body is exposed to the second gas. Again, the porous metallic layers may be platinum or other suitable material. The ceramic layers may be of any of the materials described above. Additionally, the ceramic layers may be of $Bi_2O_3$ in solid solution with either $Y_2O_3$ or $Nb_2O_5$.

The multi-layer oxygen sensor of the present invention may be constructed by a tape-casting method which includes mixing an electrolytic ceramic material with an organic binder material. The mixture is then formed into sheets which are stacked together with alternating layers of porous metallic material. Typically, the binder material is burned out of the ceramic material by heating the stack at 300° C. to 500° C. for 30 minutes to 1 hour. The heating of the stack is then increased to a final temperature of 800° C. to 1400° C. The stack is maintained at the final temperature for 30 minutes to 3 hours, and may be subjected at the same time to a pressure of 0 to 5,000 psi.

Due to the similarity in operation of an oxygen sensor of the type described herein and a fuel cell for use in converting chemical energy to electrical energy, the present invention is also well-suited for use as a fuel cell.

Accordingly, it is an object of the present invention to provide an oxygen ion conducting oxygen sensor constructed of a new electrolytic ceramic material; to provide such a sensor including multiple alternating layers of an electrolytic ceramic material and a porous metallic material; to provide such a sensor having reduced material and production costs relative to presently known sensors; to provide such a sensor having a high degree of thermal shock resistance; to provide such a sensor that has a reduced threshold operating temperature; and to provide such a sensor that may be constructed by inexpensive tape-casting methods.

Other objects and advantages of the invention will be apparent from the following description, the accompanying drawings and the appended claims.

BRIEF DESCRIPTION OF THE DRAWINGS

FIG. 3 is a graphical representation of the ionic conductivity of $NiNb_2O_6$ at several densities and of $ZrO_2 + 8\%\ Y_2O_3$ as a function of temperature;

FIG. 4 is a graphical representation of initial operating temperature of multi-layer sensor devices constructed of $NiNb_2O_6$ at one of several densities as a function of the number of layers of $NiNb_2O_6$;

DETAILED DESCRIPTION OF THE PREFERRED EMBODIMENTS

Figure 1:
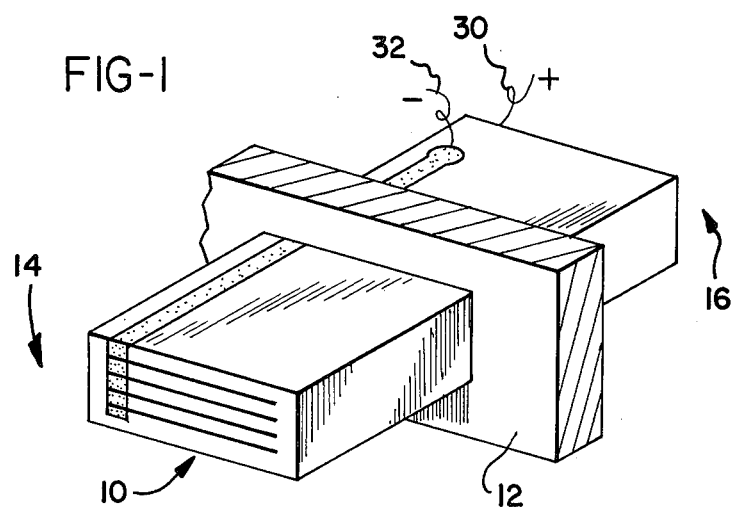
FIG. 1 is a perspective view of an oxygen sensor according to the present invention.

A preferred oxygen ion conducting ceramic material for use in the practice of the present invention is $NiNb_2O_6$. It has been found that $NiNb_2O_6$ can be formed as a dense ceramic body by mixing $Nb_2O_5$ and $NiO$, calcining for 1 to 3 hours at 800° C. to 1000° C., preferably two hours at 1000° C., and sintering for 1 to 30 hours at 1200° C. to 1400° C., preferably one hour at 1350° C. A ratio of 78.07% $Nb_2O_5$ to 21.93% $NiO$ by weight is preferred. Under the preferred conditions, the ceramic sinters with no weight loss or gain to a density of 97.2% of the theoretical density of 5.653 gm/cm³. A higher percentage of the theoretical density may be achieved using one of several methods well known in the ceramic art including, for example, a longer sintering time, finer starting particle size or hot-pressing.

Ionic conductivity measurements made on three bar samples of the $NiNb_2O_6$ ceramic material at three different densities and on a portion of a densified $ZrO_2$ plus 8% $Y_2O_3$ ceramic tube were used to obtain the data shown in FIG. 3. These data are plotted according to the ionic conductivity relation $$\sigma T = A \exp(-Q/kT) \qquad (2)$$

where $\sigma$ is the ionic conductivity, A is a constant, Q is the activation energy, and k is Boltzman's constant. The FIG. 3 data show that the ionic conductivity of $NiNb_2O_6$ increases very rapidly with increasing density and approaches the conductivity of $ZrO_2:Y_2O_3$.

The FIG. 3 data were fitted to the ionic conductivity relation set out as Eq. (2) above, and the resulting fitting parameters are given in Table I.

TABLE I

| Material | Ionic Conductivity Parameters | |
|---|---|---|
| | ln A | Q(ev) |
| $NiNb_2O_6$, 75.4% theo. density | 12.31 | 1.27 |
| $NiNb_2O_6$, 93.8% theo. density | 11.87 | 1.28 |
| $NiNb_2O_6$, 97.1% theo. density | 15.38 | 1.31 |
| $ZrO_2 + 8\%\ Y_2O_3$ | 14.30 | 1.03 |

For $ZrO_2:Y_2O_3$, the activation energy in Table I and $\sigma$-values from FIG. 3 agree well with published data. For $NiNb_2O_6$, the Table I data show that the rapid increase in $\sigma$ with density is primarily due to the rapid increase of ln A with density.

X-ray analysis of $NiNb_2O_6$ has shown that the ceramic is a single-phase, columbite structure. Consequently, it is believed that the oxygen ion conductivity is due to the oxygen vacancies in the columbite structure. The columbite structure, $AB_2O_6$ (where A and B are metal cations and O is oxygen), is obtained from the pyrochlore structure, $A_2B_2O_7$, by the removal of layers of A and O ions. In turn, the pyrochlore structure has an eighth layer of oxygen ions missing in comparison to the $A_4O_8$ fluorite structure, which has no oxygen vacancies. It will be noted that $ZrO_2$ and $CeO_2$ have the fluorite structure, and oxygen vacancies for ion conductivity must be produced by dopants such as CaO or $Y_2O_3$. No such dopants are necessary in the case of $NiNb_2O_6$.

Other ceramic materials useful in the practice of the present invention include two families of ceramics, one being the columbite structure exemplified by $NiNb_2O_6$, and the second being the pyrochlore structure exemplified by $Ni_2Nb_2O_7$. These materials are represented by the following formulas:

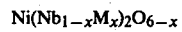

$$Ni(Nb_{1-x}M_x)_2O_{6-x}$$

and

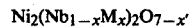

$$Ni_2(Nb_{1-x}M_x)_2O_{7-x'}$$

where M may be $Zr^{+4}$, $Ti^{+4}$, $Sn^{+4}$, $Sm^{+4}$, $Hf^{+4}$ or $Ce^{+4}$, and where x is a value from 0 to 0.2. It is noted that ionic radii considerations favor $Ti^{+4}$, $Sm^{+4}$, $Hf^{+4}$ and $Zr^{+4}$. Some of these materials may have higher ionic conductivities than $NiNb_2O_6$.

Thermal conductivity measurements performed at room temperature on a sample of the $NiNb_2O_6$ ceramic material at approximately 97% of theoretical density indicate a very large value, 0.036 cal sec$^{-1}$ cm$^{-1}$ K$^{-1}$. By way of comparison, this thermal conductivity is approximately 60% of the alumina value at room temperature which, as is well known, has one of the largest room-temperature thermal conductivities of any known non-metal.

The thermal expansion coefficient of the $NiNb_2O_6$ ceramic is $48 \times 10^{-7} K^{-1}$ at room temperature. This moderate thermal expansion coefficient combined with the large thermal conductivity value ensures thermal-shock resistance for this ceramic.

Because of the convenient sintering temperatures of the ceramic materials of the present invention (approximately 1350° C.), the ceramics can be "tape cast" into a monolithic body. As is well known in the ceramic art, tape casting is a process for making a multi-layered body (for example, a ceramic capacitor) wherein appropriate metal electrodes are interdispersed between the ceramic layers.

Figure 2:
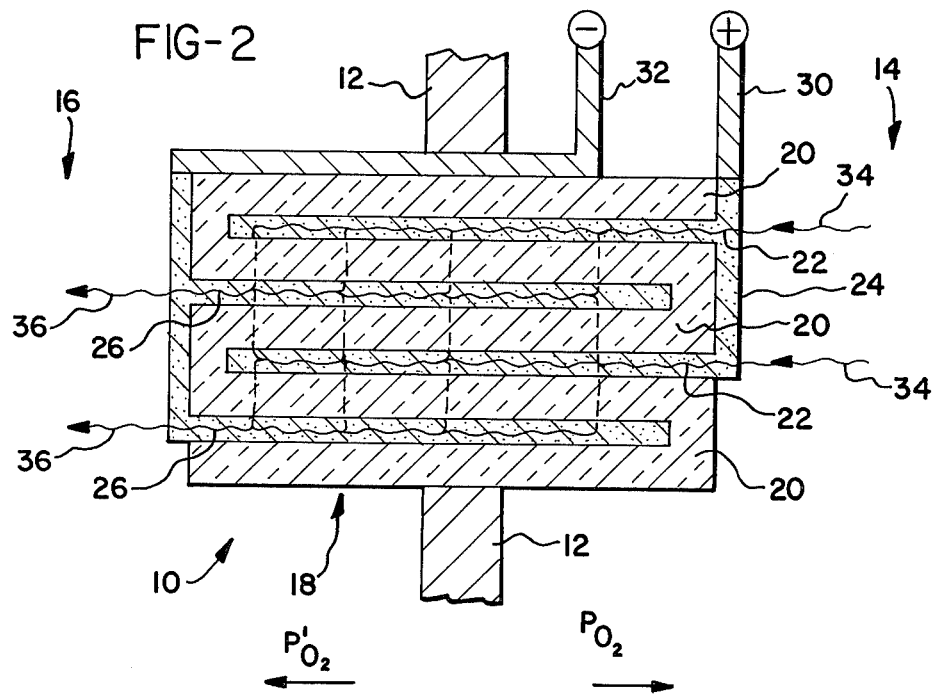
FIG. 2 is a schematic representation of the oxygen sensor.

A schematic representation of an oxygen sensor constructed according to tape-casting methods is shown in FIGS. 1 and 2. As seen in FIG. 2, an oxygen sensor 10 is shown mounted through a baffle 12 disposed so as to maintain a first gas having an oxygen partial pressure $P_{O_2}$ on the side of baffle 12 indicated generally at 14. A second gas having an oxygen partial pressure $P'_{O_2}$ less than that of the first gas is maintained on the side of baffle 12 indicated generally at 16. The sensor 10 includes a body 18 formed of alternating layers 20 of an electrolytic ceramic material and porous layers of a metallic material. Of the metallic layers, alternate layers 22 extend to a first side 24 of body 18 where they are exposed to the first gas at 14. The remaining metallic layers 26 are exposed along a second, opposing side 28 of body 18 to the second gas at 16. An electrode 30 is connected to the metallic layers 22, while an electrode 32 is connected to metallic layers 26.

The metallic layers 22 and 26 are preferably of platinum, although they may be constructed of any suitable metallic catalytic metal material. The layers 22 and 26 are fine-grained to avoid irreversible electrode effects, and are sponge-like to permit very rapid oxygen transport within the electrode layers. The oxygen contained within the first and second gases diffuses into the metallic layers as indicated by arrows 34, and thus the oxygen concentration within layers 22 corresponds to the concentration within the first gas, and the oxygen concentration within layers 26 corresponds to that of the second gas. Consequently, the oxygen ion concentrations at any two opposing metallic layers are different, and an EMF is developed by the oxygen ions diffusing across the separated ceramic layers 20. The gaseous oxygen resulting in metallic layers 26 then diffuses into the second gas along the path shown by arrows 36.

In essence, therefore, the oxygen sensor 10 consists of N galvinic cells connected in parallel, where N is the number of ceramic layers. The voltage output signal across electrodes 30 and 32 may be calculated through use of the Nernst equation set out above as Eq. (1).

Due to the temperature dependence of the Nernst relationship, it will be seen that some means for determining the temperature of the oxygen sensor must be provided to interpret the EMF generated by the sensor properly. This may be accomplished, for example, either by using standard thermocouple methods or by silk-screening a Pt+Pt−20% Rh thermocouple joint directly into the multi-layered device.

The multi-layer sensor is preferably constructed by a tape-casting technique. A powdered electrolytic ceramic material of approximately one micron grain size is mixed with an appropriate organic binder and prepared into a film sheet, preferably of 0.003 inch (0.0075 cm) thickness. A platinum layer is silk-screened onto the sheet, and a predetermined number of such sheets are stacked. The stack is heated at 250° C. to 400° C. for 2 to 30 hours, preferably 290° C. for 28 hours, so as to completely burn out the binder material. At the same time, pressure of 0 to 200 psi is applied to the stack to aid in holding it together. The heating of the stack is then increased, preferably at approximately 150° C. per hour, to a final temperature of 1200° C. to 1400° C. (preferably 1320° C.), at which the stack is held for 30 minutes to 3 hours at an applied pressure of 0 to 5000 psi.

One major criterion of an oxygen sensor is the threshold operating temperature, defined as that temperature to which the device must be heated so that the internal resistance of the oxygen sensor is sufficiently below the external load resistance that the sensor output signal can be processed. For $ZrO_2$ plus 8% $Y_2O_3$, the threshold operating temperature is approximately 600° C.

For the multi-layer sensor device disclosed herein, the total internal resistance $R_t$ is $$R_t = R_c/N = d/NA\sigma \qquad (3)$$

where $R_c$ is the resistance of one layer of thickness d and metallic layer area A, $\sigma$ is the ionic conductivity of the $NiNb_2O_6$ ceramic, and N is the number of ceramic layers in the device. The threshold operating temperature for the multi-layer $NiNb_2O_6$ device may be estimated, given that 600° C. is the threshold for a $ZrO_2+8\%$ $Y_2O_3$ tube, by solving $$(R_t)_{ZrO_2} = (R_t)_{NiNb_2O_6} \quad (4)$$

The typical dimensions of a zirconia tube mentioned above (i.e., approximate diameter of ⅜ inch, wall thickness of 0.05 inches, and length of 6 inches), and the preferred thickness (0.002 inches) and an exemplary surface area (0.25 inches) of the disclosed device are used. Additionally, the data of Table I allow estimation of ln A and Q as a function of density $\rho$ by making the reasonable assumption that ln A $\alpha\rho$ and Q $\alpha\rho$ for $\rho > 90\%$ of theoretical density.

The results of these calculations are shown graphically in FIG. 4 where the temperature is estimated as a function of the number of layers N. Up to the maximum 200 layers shown in FIG. 4 is consistent with state of the art tape casting methods. The graphical representations illustrate that the $NiNb_2O_6$ multi-layer oxygen sensing device can have a significantly lower threshold operating temperature than the presently known zirconia tubes, particularly at higher ceramic densities.

It will be noted that these estimates are not particularly sensitive to the tube or multi-layer device dimensions used, and the latter dimensions are intended to be illustrative rather than restrictive. Additionally, any increased ionic conductivity for the device through the use of the alternative materials disclosed herein will result in further lowering of the threshold operating temperature of the device.

Another criterion connected with the oxygen sensor is the response time of the device. It is well known that a zirconia tube sensor responds so rapidly (on the order of nanoseconds) that electronic compensation must be employed. The quantity $$D/d^2 = \text{constant} \quad (5)$$

defines the response conditions wherein D is the diffusivity and d is the electrolyte thickness. The condition for the $NiNb_2O_6$ multi-layer device to respond in the same time as the zirconia tube is $$(D/d^2)_{NiNb_2O_6} = (D/d^2)_{ZrO_2} \quad (6)$$

Employing the Einstein relation, $$D = (k/N_o Z_i^2 E^2)T \quad (7)$$

where k is Boltzman's constant, $N_o$ is the density of mobile ions, $Z_i$ is the balance of the ionic species being transported, and e is the electronic charge, connects D and $\sigma$. Using the Table I data and Eq. (2), Eq. (6) may be solved for the respective temperatures at which the $NiNb_2O_6$ multi-layer device and $ZrO_2$ tube have the same response time. That is, from Eqs. (6) and (7), $$(D/d^2)_{NiNb_2O_6} = (D/d^2)_{ZrO_2} \quad (8)$$

The reduced $\sigma$ for $NiNb_2O_6$ is compensated for by the reduced d, and it is found that for a ceramic density of 97% of theoretical density, the $NiNb_2O_6$ multi-layer device will actually respond faster than the zirconia tube at all temperatures using the preferred layer thickness.

Figure 6:
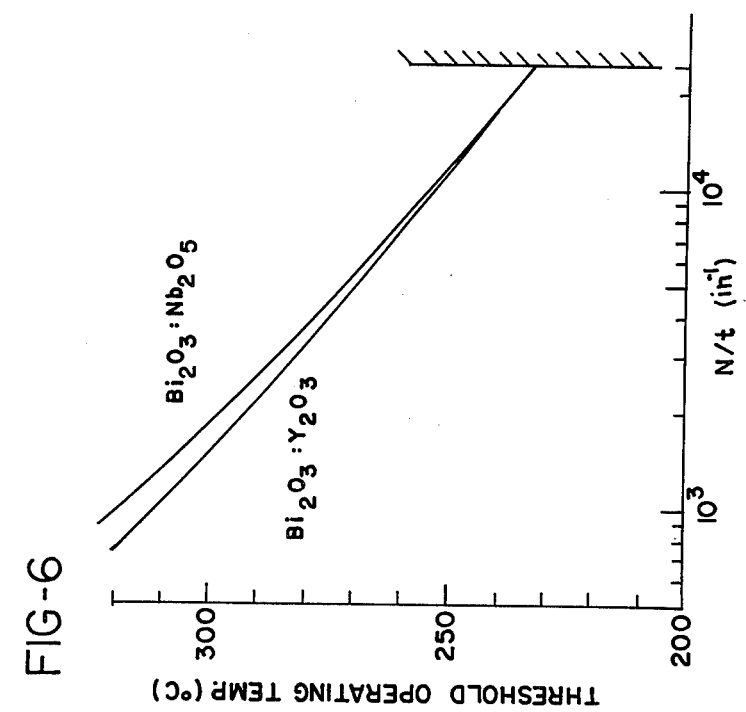
FIG. 6 is a graphical representation of initial operating temperature of multi-layer sensor devices constructed of $Bi_2O_3:Y_2O_3$ and $Bi_2O_3:Nb_2O_5$ as a function of the number of ceramic layers in the device.
Figure 5:
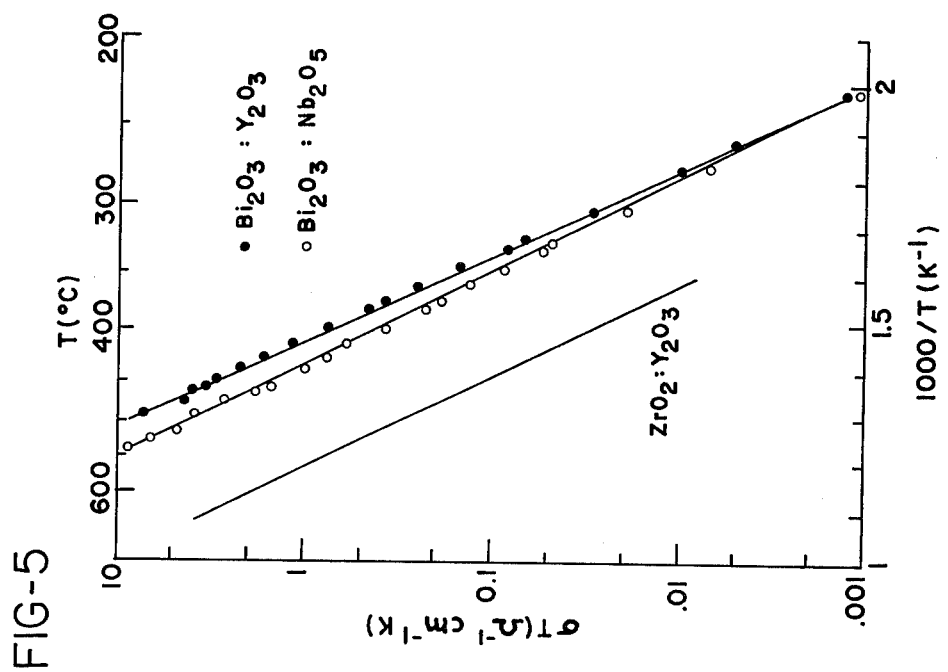
FIG. 5 is a graphical representation of the ionic conductivity of $Bi_2O_3:Y_2O_3$, $Bi_2O_3:Nb_2O_5$ and $ZrO_2:Y_2O_3$ as a function of temperature.

It will be recognized, of course, that while the above calculations concern the $NiNb_2O_6$ multi-layer sensor device, the design and construction techniques of the device may be used with any of the new ceramic materials disclosed herein. In addition, however, it has been found that $Bi_2O_3$ in solid-solution with either $Y_2O_3$ or $Nb_2O_5$ has an oxygen conductivity considerably larger than either $NiNb_2O_6$ or $ZrO_2:Y_2O_3$. Oxygen conductivity data on these materials similar to that shown in FIG. 3 is presented in FIG. 5. These $Bi_2O_3$ ceramics also have sintering temperatures low enough to permit their use with the multi-layer tape casting method described herein. Further, the threshold operating temperatures for devices constructed from these materials, calculated in the same manner as those presented in FIG. 4, are shown in FIG. 6.

Finally, it will be noted that due to the configuration of the device, the corrosion and/or erosion of the metallic layers in the multi-layer device will be considerably reduced compared to the tube devices. If necessary, however, overcoating of the exposed metallic layers with a protective, porous spinel will maintain the life of the device. Moreover, the relatively small size of the multi-layer device will allow for the addition of special exhaust-gas filtering and/or purification catalytic devices to protect the sensor. At the same time, the size of the device may be selected so that it is compatible with the fixture geometries currently used with zirconia tubes.

Those skilled in the art will readily recognize that the devices disclosed in the foregoing description are also well-suited for use as fuel cells. Such a device, for use in converting chemical energy produced by oxidation-reduction reactions in which oxygen is involved directly into electrical energy, may be constructed from materials and by methods substantially identical to those described above. Since a fuel cell of this type operates in essentially the same manner as an oxygen sensor, such a device is considered to be well within the scope of the present invention. Accordingly, the term "oxygen sensor" as used within the present application should be understood to also emcompass fuel cells.

While the forms of apparatus and the methods herein described constitute preferred embodiments of this invention, it is to be understood that the invention is not limited to these precise forms of apparatus and methods, and that changes may be made therein without departing from the scope of the invention which is defined in the appended claims.

What is claimed is:

1. An oxygen sensor for determining the oxygen partial pressure of a first gas relative to the oxygen partial pressure of a second gas, comprising:
    at least two layers of a porous metallic conductor;
    at least one layer of an electrolytic ceramic material $Ni(Nb_{1-x}M_x)_2O_{6-x}$ wherein M is selected from the group consisting of $Zr^{+4}$, $Ti^{+4}$, $Sn^{+4}$, $Sm^{+4}$, $Hf^{+4}$, $Ce^{+4}$ and mixtures thereof, and wherein x is from 0 to 0.2;
    said ceramic layer being disposed between said metallic layers and cooperating therewith to form at least a portion of a body for said sensor.

2. The sensor of claim 1 in which said ceramic material comprises $NiNb_2O_6$.

3. The sensor of claim 1 wherein said porous metallic conductor is platinum.

4. An oxygen sensor, comprising:
- at least two layers of a porous metallic conductor;
- at least one layer of an electrolytic ceramic material $Ni_2(Nb_{1-x}M_x)_2O_{7-x}$ wherein M is selected from the group consisting of $Zr^{+4}$, $Ti^{+4}$, $Sn^{+4}$, $Sm^{+4}$, $Hf^{+4}$, $Ce^{+4}$ and mixtures thereof, and wherein x is from 0 to 0.2;
- said layer of ceramic material being disposed between said layers of said porous metallic conductor and cooperating therewith to form at least a portion of a body for said sensor;
- a first electrode connected to a first of said layers of said porous metallic conductor; and
- a second electrode connected to a second of said layers of said porous metallic conductor.

5. A sensor for determining the oxygen partial pressure of a first gas relative to the oxygen partial pressure of a second gas, said first and second gases being maintained in separate relationship, the sensor comprising:
- a plurality of layers of an electrolytic ceramic material;
- a plurality of layers of a porous metallic conductor;
- each of said layers of porous metallic conductor being interposed between and contained by two of said layers of ceramic material so as to form a solid body of alternating ceramic and metallic layers, said body having first and second opposing sides;
- first alternate ones of said layers of porous metallic conductor being exposed along said first side of said body;
- second alternate ones of said layers of porous metallic conductor being exposed along said second side of said body;
- a first electrode connecting said first alternate metallic layers; and
- a second electrode connecting said second alternate metallic layers;
- said body being adapted to be disposed such that said first side of said body is exposed to said first gas, and said second side of said body is exposed to said second gas.

6. The sensor of claim 5 wherein said metallic layers are platinum.

7. The sensor of claim 5 wherein said ceramic layers are $NiNb_2O_6$.

8. The sensor of claim 5 wherein said ceramic layers are $Bi_2O_3$ in solid solution with $Y_2O_3$.

9. The sensor of claim 5 wherein said ceramic layers are $Bi_2O_3$ in solid solution with $Nb_2O_5$.

10. The sensor of claim 5 wherein said ceramic layers are $$Ni(Nb_{1-x}M_x)_2O_{6-x}$$

and M is selected from the group consisting of $Zr^{+4}$, $Ti^{+4}$, $Sn^{+4}$, $Sm^{+4}$, $Hf^{+4}$, $Ce^{+4}$, and mixtures thereof, and x is from 0 to 0.2.

11. The sensor of claim 5 wherein said ceramic layers are $$Ni_2(Nb_{1-x}M_x)_2O_{7-x}$$

and M is selected from the group consisting of $Zr^{+4}$, $Ti^{+4}$, $Sn^{+4}$, $Sm^{+4}$, $Hf^{+4}$, $Ce^{+4}$, and mixtures thereof, and x is from 0 to 0.2.

12. A fuel cell for converting chemical energy released by reaction between a first gas and a second gas into electrical energy, said first and second gases being maintained in separate relationship, comprising:
- a plurality of layers of an electrolytic ceramic material;
- a plurality of layers of porous metallic conductor;
- each of said layers of porous metallic conductor being interposed between and contained by two of said layers of ceramic material so as to form a solid body of alternating ceramic and metallic layers, said body having first and second opposing sides;
- first alternate ones of said layers of porous metallic conductor being exposed along said first side of said body;
- second alternate ones of said layers of porous metallic conductor being exposed along said second side of said body;
- a first electrode connecting said first alternate metallic layers; and
- a second electrode connecting said second alternate metallic layers;
- said body being adapted to be disposed such that said first side of said body is exposed to said first gas, and said second side of said body is exposed to said second gas.

13. The fuel cell of claim 12 wherein said metallic layers are platinum.

14. The fuel cell of claim 12 wherein said ceramic layers are $NiNb_2O_6$.

15. The fuel cell of claim 12 wherein said ceramic layers are $Bi_2O_3$ in solid solution with $Y_2O_3$.

16. The fuel cell of claim 12 wherein said ceramic layers are $Bi_2O_3$ in solid solution with $Nb_2O_5$.

17. The fuel cell of claim 12 wherein said ceramic layers are $$Ni(Nb_{1-x}M_x)_2O_{6-x}$$

and M is selected from the group consisting of $Zr^{+4}$, $Ti^{+4}$, $Sn^{+4}$, $Sm^{+4}$, $Hf^{+4}$, $Ce^{+4}$, and mixtures thereof, and x is from 0 to 0.2.

18. The fuel cell of claim 12 wherein said ceramic layers are $$Ni_2(Nb_{1-x}M_x)_2O_{7-x}$$

and M is selected from the group consisting of $Zr^{+4}$, $Ti^{+4}$, $Sn^{+4}$, $Sm^{+4}$, $Hf^{+4}$, $Ce^{+4}$, and mixtures thereof, and x is from 0 to 0.2.

* * * * *